United States Patent [19]

Farmer et al.

[11] 4,273,431
[45] Jun. 16, 1981

[54] ADAPTER FOR COUPLING A PHOTOGRAPHIC CAMERA WITH A VIEWING DEVICE

[75] Inventors: Zane M. Farmer, Ashburnham; Edward A. Yobaccio, Westwood, both of Mass.

[73] Assignee: Polaroid Corporation, Cambridge, Mass.

[21] Appl. No.: 63,254

[22] Filed: Aug. 2, 1979

[51] Int. Cl.³ .............. G03B 7/087; G03B 17/48; A61B 1/04
[52] U.S. Cl. ............... 354/59; 354/60 R; 354/62; 354/79; 354/269
[58] Field of Search ............ 354/22, 23 R, 60 R, 354/62, 63, 79, 269, 49, 59, 42; 350/19; 128/4, 6-8

[56] References Cited

U.S. PATENT DOCUMENTS

| | | |
|---|---|---|
| 3,292,490 | 12/1966 | Moore . |
| 3,623,807 | 11/1971 | Gabler ............................ 350/19 X |
| 3,641,898 | 2/1972 | Kawahara . |
| 3,696,720 | 10/1972 | Vinson . |
| 3,721,170 | 3/1973 | Johnson . |
| 3,798,665 | 3/1974 | Eloranta . |
| 3,898,678 | 6/1975 | Walworth ............................ 354/79 |
| 3,900,858 | 8/1975 | McCann et al. ..................... 354/79 |
| 3,999,195 | 12/1976 | Little ................................. 354/60 L |
| 4,021,825 | 5/1977 | McCann et al. ..................... 354/79 |
| 4,157,216 | 6/1979 | Plummer ............................ 354/62 |
| 4,192,597 | 3/1980 | Ting ................................. 354/62 X |

Primary Examiner—L. T. Hix
Assistant Examiner—William B. Perkey
Attorney, Agent, or Firm—Francis J. Caufield

[57] ABSTRACT

An adapter is provided by which a self-contained automatic camera can be coupled to an optical viewing device such as an endoscope to view and photograph an image formed by the viewing device while advantageously preserving an automatic exposure feature of the camera to control exposure.

14 Claims, 8 Drawing Figures

ADAPTER FOR COUPLING A PHOTOGRAPHIC CAMERA WITH A VIEWING DEVICE

BACKGROUND OF THE INVENTION

1. Field of the Invention

This invention in general relates to photography and in particular to an adapter by which a self-contained automatic camera can be coupled to an optical viewing device such as an endoscope to photograph an image formed by the eyepiece of the viewing device in a manner whereby an automatic exposure control feature of the camera is preserved.

2. Description of the Prior Art

Photographic cameras of the type which include systems by which exposure of a film is automatically controlled in a predetermined manner are well-known in the prior art. In general, such exposure control systems usually comprise an electromechanical shutter arrangement that is controlled by the output of a scene brightness measuring system in such a way that aperture and/or shutter speed are set in accordance with a film's given speed rating and what the scene brightness measuring system judges the "average" scene brightness to be.

Also well-known to the prior art are optical viewing devices such as microscopes, telescopes, binoculars, and endoscopes—all instruments useful for their ability to permit visualization of details in objects which would otherwise be too distant, small, dim or inaccessible for the unaided eye to see.

Obtaining permanent photographic records of what the eye sees through such optical viewing devices is an established practice having obvious scientific and artistic benefits. Like others, however, this photographic practice requires, among other things, that the image of the object to be photographed be available for observation immediately prior to and preferably during exposure and also must be properly exposed to record important details in the object—particularly in medical applications like endoscopic photography. These requirements are generally difficult to satisfy especially where the camera includes an automatic exposure control system as described above and does not have a reflex viewing arrangement where the image can be observed directly through the camera objective lens.

Consequently, using a camera with automatic exposure control to photograph images formed by such optical viewing devices requires that the automatic exposure control be bypassed or overridden in some way or alternatively be coupled with the viewing device in such a way that the brightness of the image formed by the viewing device can be measured by the brightness measuring system of the camera. The alternative above, while advantageous because it preserves the camera automatic exposure control feature, presents a major problem since the viewing device image is generally hidden from the view of the camera brightness measuring system. This usually comes about because of an offset between the camera objective lens, which is generally optically aligned with the viewing device image, and the optical axis of the camera brightness measuring system. Moreover, unless the camera includes a reflex viewing device, such as those of the single lens reflex or twin reflex lens type camera, the problem becomes aggravated.

Some prior art arrangements for coupling automatic exposure control systems of self-contained cameras with optical viewing devices show arrangements by which some part of the useful light intended for the photographic image is diverted to the photodetector of the camera automatic exposure control system through the use of branched light paths which typically utilize beamsplitters, fiber optic bundles or similar optical elements. Typical of such arrangements are those shown, for example, in U.S. Pat. No. 3,641,898 issued to Ichizo Kawahara on Feb. 15, 1972 and entitled "Electrically Driven Camera For An Endoscope"; U.S. Pat. No. 3,721,170 issued to Bruce K. Johnson on Mar. 20, 1973 and entitled "Apparatus For Adapting A Reflex Camera For Use With A Monocular Microscope"; U.S. Pat. No. 3,292,490 issued to Kenneth M. Moore on Dec. 20, 1966 and entitled "Photographic Equipment"; and U.S. Pat. No. 3,798,665 issued to Vaito K. Eloranta et al. on Mar. 19, 1974 and entitled "Apparatus For Adapting A Reflex Camera To Use With A Binocular Microscope".

Other prior art arrangements show apparatus by which a part of the image light not intended for the photographic image, but representative of the brightness of the viewing device image, is diverted to the camera automatic exposure control system photodetector or light sensing element. Such arrangements are similar to those shown, for example, in U.S. Pat. No. 3,898,678 issued to Vivian K. Walworth on Aug. 5, 1975 and entitled "Camera To Microscope Adapter With Means For Operating An Exposure Control" and U.S. Pat. No. 3,900,858 issued to Mary Conlin McCann et al. on Aug. 19, 1975 and entitled "Camera To Microscope Adapter With Special Optical Element".

None of the known prior art arrangements, however, appear to show means by which a self-contained automatic camera with a non-through-the-lens viewing device can be coupled with an optical viewing device to photograph and view an image formed thereby while making use of the camera's automatic exposure control system. Therefore, the foregoing is a primary object of the present invention. Other objects of the invention will in part be obvious and will in part appear hereinafter. The invention accordingly comprises the apparatus possessing the construction, combination of elements and arrangement of parts which are exemplified in the following detailed disclosure.

SUMMARY OF THE INVENTION

This invention in general relates to photography and in particular to an adapter for optically and mechanically coupling a photographic camera to the proximal end of an optical viewing device such as an endoscope so that the image formed by the optical viewing device can be viewed and photographed. The camera is of the type which includes an exposure control system having a light sensing system and which, upon actuation, automatically regulates the exposure delivered to a film in accordance with the speed rating of the film and the amount of light received by the light sensing system of the camera exposure control system, and the optical viewing device is of the type which has an eyepiece located at its proximal end for forming a viewable image of the object and includes means by which the object can be illuminated.

The adapter of the invention comprises a housing section for forming a releasable generally light-tight mechanical connection with the proximal end of the optical viewing device. The housing section is structured to form a branched light path having a primary branch the entrance of which optically aligns with the optical viewing device eyepiece when the housing section is connected thereto and along which the viewable image formed by the eyepiece can be directly viewed through the exit of the primary branch. The housing section also has a secondary branch depending from the the primary branch at a predetermined angle.

Also included are optical means disposed in the housing section for receiving light traveling along the primary light path branch and directing a portion of it into and along the secondary light path branch so that the viewable image formed by the eyepiece can be photographed through the exit of the secondary light path branch.

Means are provided for releasably attaching the camera to the adapter housing section so that the camera objective lens is aligned in a predetermined manner with the exit of the secondary light path branch for purposes of photographing the eyepiece viewable image while the camera light sensing system is not aligned with the secondary light path branch exit.

Additionally provided are light detecting means arranged along the adapter housing section branched light path for movement between a first arrangement in which the light detecting means provides an output signal having an electrical characteristic which varies in a predetermined manner with the brightness of the eyepiece viewable image and in which the viewable image is visually unobstructed when observed along the primary light path branch and a second arrangement in which both the primary and secondary light path branches are unobstructed so that the eyepiece viewable image can be simultaneously viewed and photographed.

Control means including circuit means are included for monitoring the light detecting means output signal while the light detecting means is in its first arrangement and determining an exposure parameter value which is appropriate for the film speed and the brightness of the eyepiece viewable image, for displacing the light detecting means from its first to its second arrangement, for actuating the camera to begin its exposure cycle, and for presenting to the camera light sensing system an artificial source of illumination to terminate the camera exposure cycle in accordance with the exposure parameter value.

DESCRIPTION OF THE DRAWINGS

The novel features that are considered characteristic of the invention are set forth with particularity in the appended claims. The invention itself, however, both as to its organization and method of operation together with other objects and advantages thereof will best be understood from the following description of the illustrated embodiment when read in connection with the accompanying drawings wherein like numbers have been employed in the different figures to denote the same parts and wherein:

DESCRIPTION OF THE PREFERRED EMBODIMENT

Figure 1:
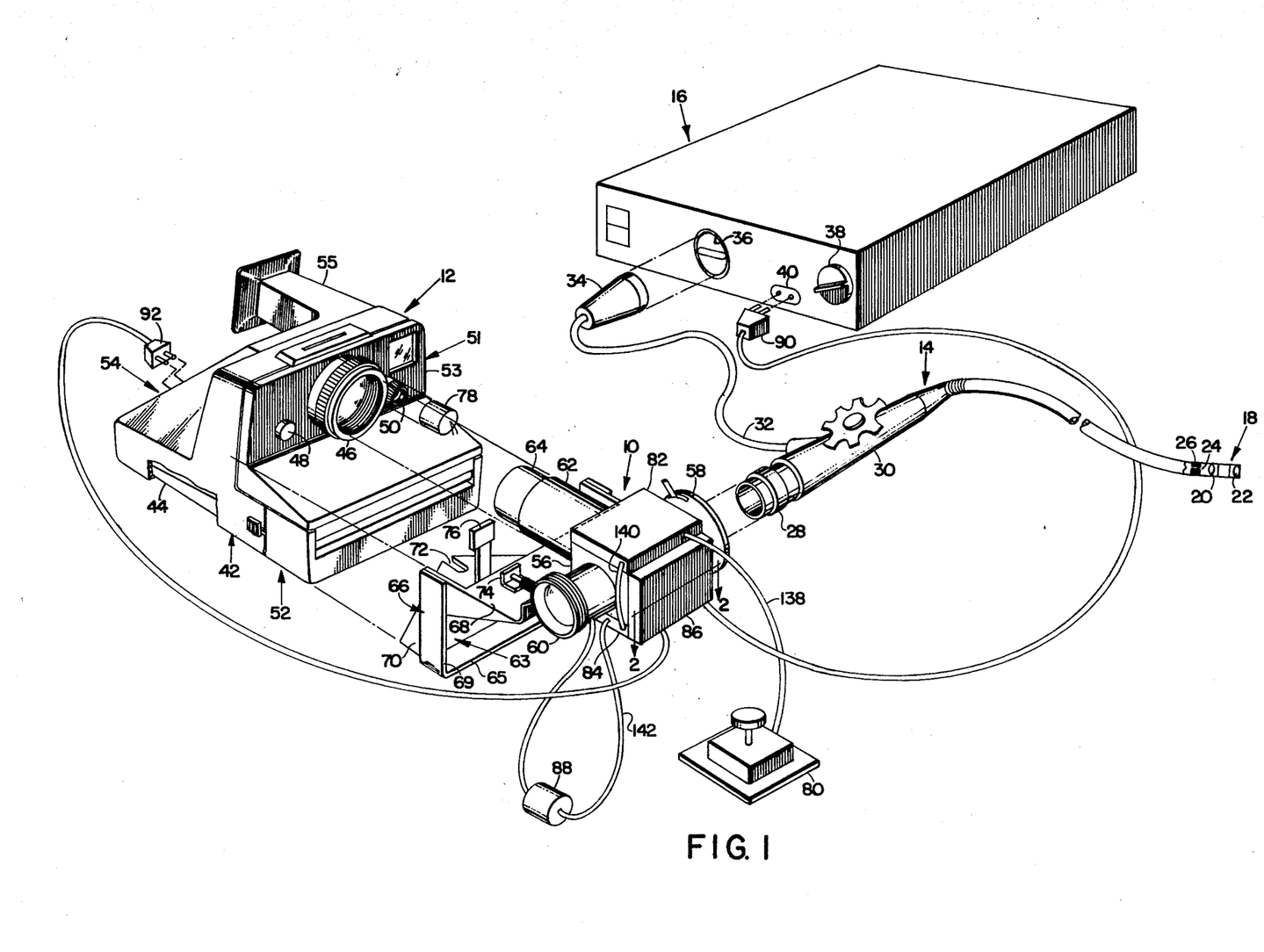
FIG. 1 is a diagrammatic perspective view of the preferred embodiment of the invention shown in combination with a photographic camera, an endoscope, and an artificial light source.

Referring now to FIG. 1, there is shown generally at 10 an adapter which is the preferred embodiment of the present invention. The adapter 10 is shown in combination with a camera 12, a clinical endoscope 14, and an electronic artificial light source 16 which collectively form a photographic system for practicing endoscopic photography in a manner which will be more readily apparent in the description that follows.

The clinical endoscope 14 constitutes an optical viewing device which is long in relation to its diameter and has a field of view that is larger than the diameter through which the field can be seen. Because the endoscope 14 is rather long, the field which it is used to view is inherently spaced several diameters away from the aperture through which it is viewed. As best shown in FIG. 1, the endoscope 14 comprises an elongated flexible fiber optic bundle 26 which has an objective lens system 18, comprising a pair of spaced apart doublets 20 and 22 respectively, for forming on a distal face 24 of the fiber optic bundle 26 a real image of the object or field being explored by an examining physician. The image formed on the fiber optic bundle face 24 is then transferred in a well-known manner via the fiber optic bundle 26 to the proximal end of the endoscope 14 where it is then reimaged by an eyepiece 28 which forms a collimated or nearly collimated image of the object which is located at the distal end of the endoscope 14.

An object under examination is illuminated via another fiber optic bundle 32 which receives light at its proximal end from a lamp assembly generally designated at 36 in the light source 16. The lamp assembly 36 can be operated in a well-known manner in a steady state mode to provide a continuous source of illumination which is optically coupled in a well-known manner with the fiber optic bundle 32 via an adapter 34. The adapter 34 may include a condenser lens system for providing even illumination of the field under investigation and may also include a heat absorbing filter which cools the light to keep the distal end of the endoscope 14 at a safe operating temperature so that a patient is not endangered by excessive heat.

In addition to its continuous mode of operation, the light source 16 also operates in a strobe mode in which it produces a light pulse of given intensity and duration (see FIG. 8) in response to receiving an input switching signal via a socket 40 thereof. Immediately after receiving an input switching signal, the light source 16 automatically recharges in preparation for firing another light pulse and the time it takes to recharge is substantially shorter than the duration of the light pulse so that the light source 16 can produce a series of successive light pulses so long as the appropriate input switching signals are provided to it via the socket 40.

As is well known, a physician conducting an endoscopic examination views the interior of a patient's body organ through the eyepiece 28 until he locates what he suspects to be the site of the pathological process which may be causing the patient's disease. The purpose of the adapter 10 is to optically and mechanically couple the photographic camera 12 with the eyepiece 28 of the endoscope 14 so that the image of the field or object formed by the endoscope 14 can be viewed and photographed.

The camera 12 may be any of a number of well-known types but, as illustrated, represents Polaroid Corporation's Pronto! or similar model camera which is fully automatic having an automatic exposure control system and is adapted to accept the well-known self-processable SX-70 color film which is processed by the camera 12 in a well-known manner immediately after it has been exposed.

The camera 12 can be operated in either an ambient exposure mode in which available light provides the source for illuminating the scene or in a flash mode in which the source for illuminating the scene can either be a well-known linear photoflash array or an electronic strobe.

The camera 12 is a rigid, non-folding body type which includes a generally prismatic shaped major housing 42, a generally L-shaped front housing 51, and a generally rectangularly-shaped film loading door 52 which collectively define its outward appearance and serve to house and protect its interior components.

The base of the prismatic housing 42 is adapted in a well-known manner to releasably receive and hold a film cassette 44 in which is disposed a stacked array of self-processable film units and a flat, thin battery which is positioned underneath the array of film units (neither shown). The film cassette battery is used to supply power to operate the various electrical components of the camera 12 and may also be connected with in a well-known manner via a battery voltage receptacle (not shown) located on a rear wall of the prismatic housing 42 and generally designated at 54. An example of such film cassettes is described in considerable detail in U.S. Pat. No. 3,872,487 issued to Nicholas Gold on Mar. 18, 1975 and entitled "Photographic Film Assemblage and Apparatus" and of such self-processable film units in, for example, U.S. Pat. Nos. 3,415,644; 3,594,165; and 3,761,268.

Located in a vertical forward wall 53 of the L-shaped housing 51 is a photographic objective lens 46 which may be a Cooke Triplet or other similar multi-element type of lens which can be focused by manually adjusting the axial air spacing between its optical elements. To use the camera 12 with the adapter 10 to photograph the image formed by the endoscope eyepiece 28, the photographic objective lens 46 is set for infinity focus because the image emerging from the endoscope eyepiece 28 is collimated or nearly so.

Located within the prismatic body 42 is a trapezoidal-shaped mirror (not shown) that is arranged at a predetermined angle with respect to the optical axis of the objective lens 46 and the film cassette 44 to provide a folded light path therebetween along which image forming scene rays travel to the film within the cassette 44 during the camera exposure cycle.

The prismatic housing 42 additionally includes an integrally molded elongated section 55 which extends rearwardly and serves to house a reversed Galilean-type viewfinder (not shown) that is independent of the objective taking lens 46 and has an optical axis which is offset with respect to the optical axis of the objective taking lens 46. The viewing system of the camera 12 is thus a non-through-the-lens type which permits a photographer to aim the camera 12 to frame the subject matter of interest but does not facilitate focusing in any way.

The camera 12 is actuated by depressing a camera start button or switch 48, also located in the vertical wall 53, which couples the film cassette battery with the various electrical components of the camera 12 to initiate a photographic cycle for ambient lighting conditions during which film exposure commences after a predetermined delay upon the opening of an electromagnetically actuated mechanical shutter (not shown) and thereafter is automatically terminated from an electrical signal which is generated by a light sensing system generally designated at 50 which measures scene brightness and commands the shutter to close upon the detection of a predetermined exposure value which is appropriate for the scene lighting conditions and the speed of the film which is contained with the cassette 44. The camera exposure control system is of the type which is more fully described in, for example, U.S. Pat. No. 3,942,183 issued to George D. Whiteside on Mar. 2, 1976 and entitled "Camera With Pivoting Blades". As can be seen in the Whiteside patent, the camera shutter is actuated by an electromagnetic device in the form of a solenoid 74 which is positioned behind the front vertical wall 53 just above the camera actuator button 48 to drive a pair of pivotally mounted shutter blades of the so-called scanning aperture type (not shown) under the control of a well-known electronic circuit which includes the light sensing system 50.

Figure 2:
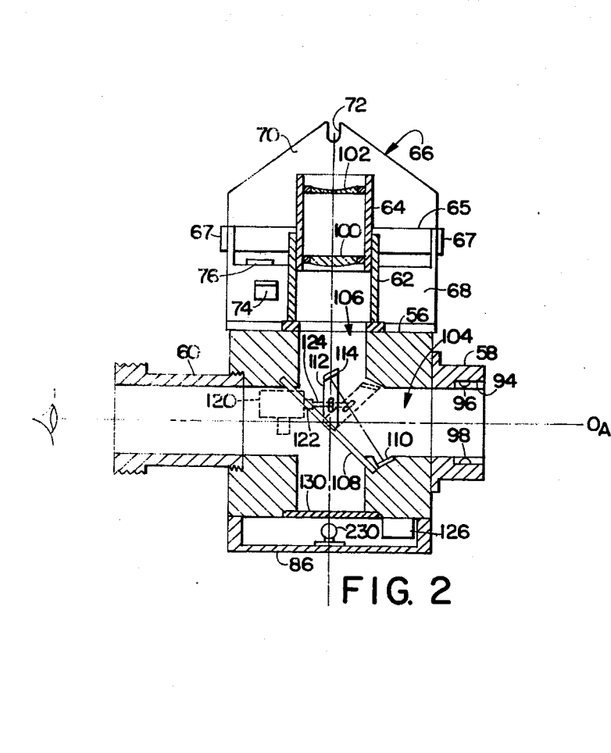
FIG. 2 is an enlarged sectional view of part of the invention taken generally along line 2—2 of FIG. 1.

Referring now to FIGS. 1 and 2, it can be seen that the adapter 10 comprises a generally parallelepiped-shaped main housing section 56 having a cylindrical bore 104 therethrough whose axis is parallel with the optical axis, OA, of the endscope eyepiece 28. The cylindrical bore 104 defines a primary branch of a branched light path of the adapter 10. A secondary branch of the adapter branched light path is defined by a second cylindrical bore 106 which extends through the housing 56 and intersects the primary branch 104 perpendicularly.

Aligned with the entrance to the primary light path branch 104 is a connector 58 which is provided with a cylindrical recess 94 in which is disposed well-known locking screws, 96 and 98. The connector 58 serves to mechanically releasably couple the proximal end of the endoscope eyepiece 28 with the adapter 10 to optically align the endoscope eyepiece 28 with the primary light path branch 104.

Provided at the exit of the primary light path branch 104 is a cylindrical eye relief piece 60 the central axis of which is coaxial with the central axis of the primary light path branch 104 and the optical axis of the endoscope eyepiece 28. With the endoscope eyepiece 28 connected with the adapter 10 via the connector 58, an observer can view the image formed by the endoscope eyepiece 28 by looking directly along the axis of the light path branch 104.

In the foregoing manner, the adapter 10 is provided with a housing section for forming a releasably generally light-tight mechanical connection with the proximal end of the endoscope eyepiece 28 and is further structured to form a branched light path having a primary branch the entrance of which optically aligns with the endoscope eyepiece 28 when the housing 56 is connected thereto via the connector 58 and along which the viewable image formed by the eyepiece 28 can be directly viewed through the exit of the primary light path branch 104 and also has a secondary light path branch 106 depending from the primary light path branch 104 at a predetermined angle.

Optical means in the form of a beamsplitter 108, arranged at 45° to the optical axis, OA, are disposed in the housing 56 for receiving light traveling along the primary light path branch 104 and directing a portion of it into and along the secondary light path branch 106 so that the viewable image formed by the endoscope eyepiece 28 can be photographed through the exit of the secondary light path branch 106.

Aligned with the exit of the secondary light path branch 106 is a cylindrical collar 62 whose central axis is coaxial with the optical axis of the endoscope eyepiece 28 which is folded by the beamsplitter 108. Slidably disposed within the collar 62 is a Galilean telescope 64 which is composed in a well-known manner of spaced apart positive and negative lenses, 100 and 102 respectively. The telescope 64, as is well known, is an afocal optical device which, in the arrangement illustrated above, is optically aligned with the exit of the secondary light path branch 106 and is structured in a well-known manner to magnify the image presented to the camera objective lens 46.

In order to assure that the intensity of the image forming light from the eyepiece viewable image 28 which reaches the camera objective lens 46 is maximized, the reflection and the transmission characteristics of the beamsplitter 108 are selected so that a major portion of the light which forms the endoscope eyepiece image is reflected into and along the secondary light path branch 106 toward the camera objective lens 46 via the telescope 64 while the remaining portion is transmitted along the primary light path branch 104 toward the exit thereof for observation by the user. In this regard, the beamsplitter 108 is preferably structured so that it reflects at least 80 percent of the light incident thereon toward the camera objective lens 46 to assure maximum intensity of the eyepiece viewable image for purposes of adequate exposure while the lesser portion of the light comprising the eyepiece image is transmitted along the primary light path branch 104. This can be done because generally the eye is much more sensitive at low light levels and therefore requires a less intense image for observation while the film sensitivity is such that it requires a much higher intensity image for photographic exposure purposes.

Referring again to FIG. 1, it can be seen that the adapter 10 includes, in the form of a frame 66, means for releasably attaching the camera 12 to the adapter housing section 56 so that the camera objective lens 46 is aligned in a predetermined manner with the Galilean telescope 64. The frame 66 is structured in such a way that the objective lens 46 is optically aligned with the exit of the secondary light path branch 106 for purposes of photographing the eyepiece viewable image. The frame 66 comprises a generally U-shaped member 69 having extending rearwardly from the base section thereof a pentagon-shaped platform member 70 (see FIG. 2) and has, extending between leg sections 67 thereof, a generally forwardly extending, gussetted, rectangularly-shaped shelf member 68 which attaches to the adapter housing 56 as best shown in FIG. 2. Between the platform member 70 and the shelf member 68 there is a space, designated generally at 63, into which the front end of the camera 12, defined by the door 52 and the generally horizontally extending shelf of the L-shaped front housing 51 thereof, fits.

The parts of the frame 66 are configured so that the camera 12 slidably inserts into the opening 63, toward the adapter 10, and is stopped when the shelf 68 strikes the surface of the camera vertical wall 53 at which time the camera objective lens 46 will be positioned laterally so that its optical axis is in alignment with the optical axis of the telescope 64. The pentagonal-shaped base 70 of the frame 66 engages with the bottom of the camera 12 and is provided with a slot 72 through which can be inserted a standard threaded bolt which is structured to fit into a tripod mount which is located in the base of the camera 12 but is not shown. Also located on the frame member shelf 68 is a bracket 74 which supports the forward end of a pneumatically operated cable release 148 (see FIG. 3) such that the end of the cable release 148 is automatically aligned with the camera actuator button 48, for purposes which will become clear hereinafter, when the camera 12 is mechanically coupled with the adapter 10. In addition, the frame member shelf 68 has depending upwardly therefrom a magnetic proximity pickup coil 76 which is automatically aligned in overlying relation to the camera shutter solenoid which is located just above the camera actuator button 48 and immediately behind the camera vertical wall 53. The purpose of the magnetic proximity pickup coil 76 will become apparent hereinafter. It should be noted that the sliding feature of the telescope 64, within the collar 62, provides a means for assuring that a generally light-tight connection between the camera objective taking lens 46 and the telescope 64 is maintained even if there are tolerance variations between the geometry of cameras and the adapter 10.

It is to be noted that the means for mechanically coupling the camera with the adapter 10 are structured so that when the camera 12 is coupled with the adapter 10, the light sensing system 50 of the camera 12 is not aligned with any portion of the adapter secondary light path branch 106 so that light which forms the endoscope viewable image is not available to the camera light sensing system 50 for automatic exposure control purposes. Therefore, for operatively coupling the camera light sensing system 50 with the endoscope eyepiece viewable image for exposure control purposes, the adapter 10 is provided with light detecting means arranged along the branched light path of the adapter housing 56 to provide an output signal which has an electrical characteristic which varies in a predetermined manner with the brightness of the eyepiece viewable image and operates in a manner which will best be understood by referring now to FIGS. 2 and 3. In those figures it can be seen that the adapter light detecting means comprises a photodetector 110 which is fixedly positioned in the primary light path branch 106, ahead of the beam-splitter 108, and is arranged so as not to directly intercept any light from the endoscope eyepiece image and is thus hidden from the view of an observer looking along the primary light path branch 106 at the endoscope eyepiece image. The photodetector 110 is preferably a silicon semiconductor device arranged to operate in a photovoltaic mode to provide the light detecting means output signal and forms part of the circuit shown in FIG. 4 which is designated generally at 126 in that figure. The manner in which the photodetector 110 cooperates with the circuit 126 will become apparent in the description of the circuit 126 to follow. Also forming part of the adapter light detecting means is a planar mirror 114 (see FIG. 3) which is fixedly mounted to a semicircular yoke 112. The yoke 112 is pivotally mounted about pivot pins 116 and 118 respectively, generally in the adapter secondary light path branch 106, for movement between a first position wherein the mirror 114 intercepts light reflected from the beamsplitter 108 and directs it onto the photodetector 110 (see FIG. 2) and a second position illustrated in phantom in FIG. 2 wherein the mirror 114, positioned as shown in phantom, is out of the path of travel of light traveling along both of the adapter light path branches, 104 and 106. As best shown in FIG. 2, the surfaces of the mirror 114 and the photodetector 110 are arranged in a parallel manner when the yoke 112 is in its first position so that a perpendicular from the centers of the surfaces of the mirror 114 and the photodetector 110 are colinear. Also, the mirror 114 is structured to have a small surface area compared to the cross sectional area of the second light path branch 106 whereby it is structured to intercept only a given percentage of the central beam of light reflected from the beamsplitter 108 when the yoke 112 is in its first position. The yoke 112 is moved between its first and second positions by a pneumatic cylinder 120 (see FIG. 3) through the use of a connecting rod 124 which has one end attached to the yoke 112 and the other end attached to a piston 122 of the cylinder 120. The manner in which the cylinder 120 operates will be discussed in detail hereinafter.

In the foregoing manner, the adapter 10 is provided with light detecting means arranged along the adapter housing branched light path for movement between a first arrangement in which the light detecting means provides an output signal having an electrical characteristic which varies in a predetermined manner with the brightness of the eyepiece viewable image and in which the viewable image is visually unobstructed when observed along the primary light path branch 104 and a second arrangement in which both the primary light path branch and the secondary light path branch, 104 and 106 respectively, are unobstructed so that the eyepiece viewable image can be simultaneously viewed and photographed.

Figure 3:
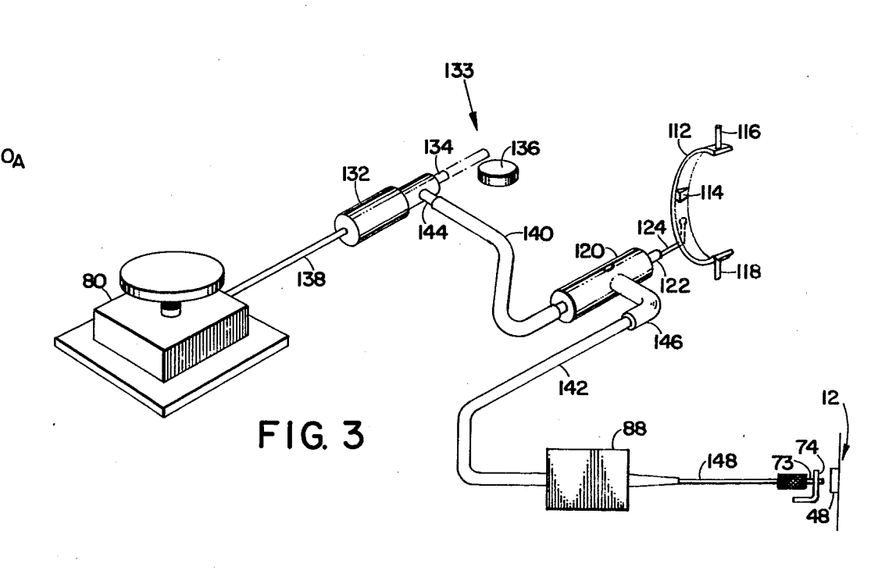
FIG. 3 is an enlarged diagrammatic perspective view of part of the invention of FIG. 1.
Figure 4:
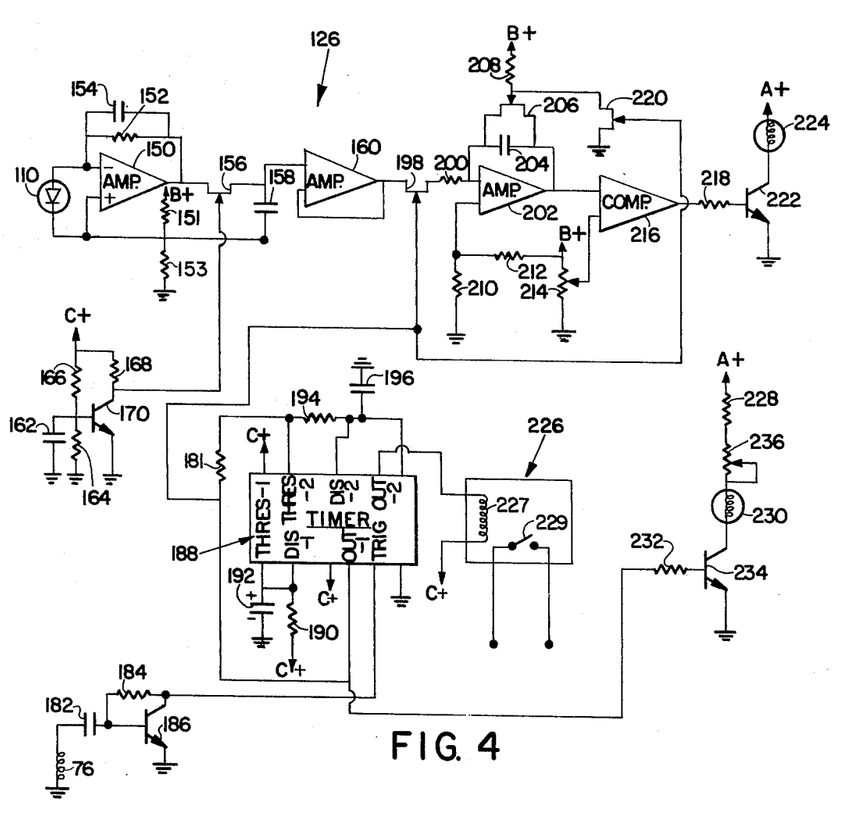
FIG. 4 is a circuit diagram of part of the invention of FIG. 1.

Control means comprising a pneumatic system generally designated at 133 in FIG. 3 and the circuit 126 are provided for monitoring the output signal of the photodetector 110 while the light detecting means is in its first arrangement as illustrated in FIG. 2 and determining an exposure parameter value which is appropriate for the film speed and the brightness of the eyepiece viewable image, for displacing the light detecting means from its first to its second arrangement, for actuating the camera 12 to begin its exposure cycle, and for presenting to the camera light sensing system 50 an artificial source of illumination to terminate the camera exposure cycle in accordance with the exposure parameter value.

Referring now to FIGS. 1, 2 and 3, it can be seen that the pneumatic system 133 comprises a manually actuable pneumatic actuator 80 which operates in a well-known manner when actuated to provide a positive pressure at its outlet which is connected with an airline 138. The airline 138 is connected to the inlet of a cylinder 132 and an exit 144 of the cylinder 132 is connected to an airline 140 which is connected to the inlet of the pneumatic cylinder 120. An outlet 146 of the cylinder 120 is connected to an airline 142 which in turn is connected with the inlet of another cylinder 88.

The cylinder 132 is physically located in a cylinder housing 82 (FIG. 1) which is attached to the adapter housing 56 while the cylinder 120 is located in a cylinder housing 84 which is also attached to the adapter housing 56.

Arranged in a well-known manner within the cylinder 88 is a conventional cable release 148 which is attached in a conventional way to the bracket 74 located on the forward frame shelf 68 as shown in FIG. 1.

The cylinder 132 is provided in a well-known manner with a piston 134 which responds to the positive pressure from the actuator 80 to first displace the piston 134 from its position shown in solid lines in FIG. 3 to a second position illustrated in phantom in FIG. 3 wherein the piston 134 interrupts the magnetic field of a permanent magnet 136 which forms part of a magnetic reed switch for purposes which will become apparent hereinafter.

The piston 122 of the cylinder 120 is also moved in a well-known manner from a first position wherein the yoke 112 is positioned as shown in solid in FIG. 2 to a second position to move the yoke 112 to its position illustrated in phantom in FIG. 2 but only after the piston 134 has been moved from its first position to its second position.

The cable release 148 is moved by the pneumatic cylinder 88 from its position illustrated in FIG. 3 to a position wherein a push rod member 73 thereof is brought into engagement with the camera actuator button 48 but only after the yoke 112 has been moved from its first to its second position.

Figure 6:
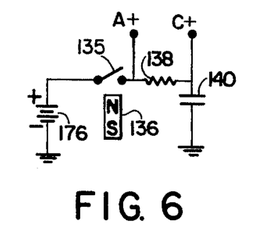
FIG. 6 is a diagram of a circuit which is used in conjunction with the circuit of FIG. 4.

Referring now to FIG. 6, there is shown a power supply circuit which comprises a battery 176 which is located in the film cassette 44. A reed switch 135 and the permanent magnet 136 collectively form a magnetic reed switch. The switch 135 has one terminal connected to the positive side of the battery 176 and another terminal coupled to a resistor 138. The other terminal of the resistor 138 is coupled in common with the positive terminal of a capacitor 140 while the negative terminal of the capacitor 140 is connected with ground. The circuit illustrated in FIG. 6 has in addition two terminals labeled A+ and C+ which provide power to various points in the circuit 126 as shown in FIG. 4.

Electrical connection with the film cassette battery 176 is made via a plug (see FIG. 1) 92 which inserts into the camera socket 54 in a well-known manner to supply power to the circuit of FIG. 6.

Figure 5:
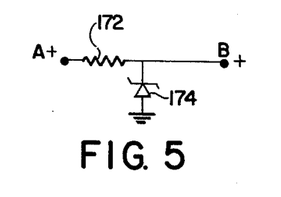
FIG. 5 is a diagram of a well-known voltage regulating circuit.

Referring now to FIG. 5, there is shown a voltage regulating circuit comprising a resistor 172 and a zener diode 174 which are arranged in series across the A+ terminal of the circuit of FIG. 6 to provide a regulated voltage which is supplied to various points of the circuit 126 as illustrated in FIG. 4. The resistor 172 and the zener diode 174 operate in a conventional manner to maintain voltage at a terminal labeled B+ in FIG. 5 at a constant value should variations in the voltage of the battery 176 occur.

The manner in which voltage is supplied at the terminals labeled A+, B+ and C+ is as follows. The piston 134 of the cylinder 132 in moving from its first position to its second position passes by the permanent magnet 136 of the magnetic reed switch of FIGS. 1 and 6 interrupting its magnetic field to close the terminals of the switch 135 thereby making available the voltage of the battery 176 at the terminals labeled A+ and C+ of the circuit of FIG. 6. The resistor 138 and the capacitor 140 operate in a well-known manner as a low band-pass filtering system to reduce the effects of contact bounce in the magnetically actuated reed switch 135 and also operate to lower the AC impedance at the terminal labeled C+ of FIG. 6.

In the foregoing manner, the pneumatic system 133 in combination with the reed switch 135 operate to supply power to the circuit 126 while the light detecting means of the adapter is in its first arrangement and thereafter operates to move the light detecting means into its second arrangement and then to initiate the photographic exposure cycle of the camera via the pneumatically actuated cable release 148 after the adapter light detecting means has been moved to its second arrangement.

The purpose of the circuit 126, in general, is to monitor the output signal of the photodetector 110 while the adapter light detecting means is in its first arrangement and determine an exposure parameter value which is appropriate for the film speed and the brightness of the eyepiece viewable image and then to present to the camera light sensing system 50 an artificial source of illumination to terminate the camera exposure cycle in accordance with the exposure parameter value. The nature and operation of the circuit 126 will best be understood with reference to FIG. 4 wherein it is seen that the photodetector 110 has its cathode connected with the negative terminal of a conventional operational amplifier 150 while the anode of the photodetector 110 is connected with the positive input terminal of the amplifier 150, to ground via a resistor 153, which is part of a voltage dividing network which also includes a resistor 151, and to the negative side of a capacitor 158. The anode of the photodetector 110 is also coupled in common with one end of a resistor 152 whose other end is connected with the output of the amplifier 150 thus serving as a feedback resistor for the amplifier 150. Connected in parallel with the feedback resistor 152 is a capacitor 154 which operates in a conventional manner to filter out AC components from the output of the photodetector 110.

Arranged in the foregoing manner, the photodetector 110, the operational amplifier 150, the feedback resistor 152 and the filter capacitor 154 cooperate to provide an output signal at the output side of the operational amplifier 150. The output signal has an electrical characteristic in the form of a voltage which varies in a predetermined manner in accordance with the brightness of the viewable image when the photodetector 110 is subjected to light from the image which impinges on its photosensitive surface while the adapter light detecting means is in its first arrangement.

One base of a conventional FET switch 156 is connected in common with the output of the amplifier 150 and the feedback resistor 152 while the other base of the FET switch 156 is connected in common with the positive end of the capacitor 158. The gate of the FET switch 156 is connected in common with one end of a resistor 168 and the collector of a conventional NPN transistor 170. The FET switch 156 is arranged so that it is normally closed and is opened in response to receiving a bias voltage when the transistor 170 is turned on in response to the charging of a conventional RC timing circuit which is comprised of a resistor 166, a resistor 164, and a capacitor 162. The base of the transistor 170 is connected in common with the positive end of the capacitor 162 and in common with the resistors 164 and 166 while the emitter of the transistor 170 is connected with ground. The values of the resistors 164 and 166 and the capacitor 162 are chosen to provide a timed delay after which the transistor 170 is switched on to provide the bias voltage to open the FET switch 156.

With the FET switch 156 closed, the capacitor 158 charges to the voltage output of the amplified photodetector voltage. The value of the capacitor 158 is chosen so that this happens substantially simultaneously when power is applied to the circuit 126 while the value of the timed delay provided by the aforementioned RC circuit is chosen to open the FET switch 156 prior to the yoke 112 being moved from its first position to its second position prior to actuating the camera exposure cycle.

A high impedance buffer amplifier 160 is provided having the positive end of the capacitor 158 connected to one of its input terminals and its output connected to the other input terminal. Arranged in this manner the amplifier 160 assures no leakage from the capacitor 158 when the FET switch 156 is opened. Consequently, the foregoing arrangement provides a means for sensing the brightness of the image formed by the endoscope eyepiece 28 and for storing an exposure parameter related signal corresponding to the image brightness prior to the actuation of the camera.

The output of the amplifier 160 is connected in common with one base of another conventional FET switch 198 which is arranged to be normally closed. The other base of the FET switch 198, via a resistor 200, is connected in common with the positive side of a capacitor 204 and one input terminal of another conventional operational amplifier 202. The gate of the FET switch 198 is connected to a terminal labeled OUT-1 of a well-known dual timer 188 that is structured to operate in a monostable and astable mode of operation. The normally open FET switch 198 is closed in response to receiving at its gate a logic 1 signal from the terminal of the timer labeled OUT-1.

The negative terminal of the capacitor 204 is connected in common with the output of the amplifier 202 and one input terminal of a conventional comparator 216 and is arranged in a conventional feedback manner to operate as an integrator in combination with the amplifier 202. The other terminal of the amplifier 202 is connected to ground via a resistor 210. Connected across the positive and negative terminals of the capacitor 204 are the bases of yet another conventional FET switch 206. The gate of the FET switch 206 is connected to B+ via resistor 208 and in common with one base of another, normally opened, conventional FET switch 220. The other base of the FET switch 220 is connected to ground and its gate is connected to the output terminal of the timer 188 labeled OUT-1. With the FET switch 208 normally opened and the FET switch 220 normally closed, the capacitor 204 is free to charge. However, the FET switches 208 and 220 are arranged so that, when a logic 1 signal is received from the terminal of the timer 118 labeled OUT-1 at the gate of the FET switch 220, the FET switch 220 which is normally opened is arranged to close and the FET switch 208 which is normally closed is arranged to open. However, when the logic 1 signal at the base of the FET switch 220 is removed, that switch returns to its normally open position while the FET switch 208 returns to its normally closed position thereby providing a means for discharging the capacitor 204.

The comparator 216 has its other terminal connected to B+ via a variable resistor 214 which is provided to set a voltage comparison level in the comparator 216 with which the integrated voltage on the capacitor 204 is compared in a well-known manner. The internal voltage comparison level of the comparator 216 is selected to correspond to an exposure parameter which is appropriate for the speed of the film, the brightness of the endoscope viewing image, and the performance characteristics of the shutter of the camera 12. The variable resistor 214 may be changed as is well known to accommodate films whose speeds are different thus enabling the performance of the circuit 126 to be altered in such a way so as to accommodate a range of films having different speed characteristics.

The output of the comparator 216 which is connected to the base of a conventional NPN transistor 222 via a resistor 218 is arranged to produce a logic 1 (high voltage) signal when the voltage on the capacitor 204 reaches the level of the internally set comparison voltage of the comparator 216.

The collector of the transistor 222 is connected in series with a lamp 224 which in turn is connected with A+ while the emitter of the transistor 222 is connected to ground. A logic 1 output from the comparator 216, with this arrangement, causes the transistor 222 to be turned on thus causing a current to be conducted through the lamp 224 to provide a high intensity light pulse. The lamp 224 is internally disposed in an opaque housing 78 (see FIG. 1) which is configured to slip over the camera light sensing system 50 to initially preclude any light from entering the camera light sensing system 50 so that when the camera 12 is actuated its exposure cycle is initiated and the exposure of the film commences and continues so long as light is precluded from entering the camera light sensing system 50. In this manner a high intensity light pulse from the lamp 224 is provided within the housing 78 to cause the camera light sensing system 50 to terminate exposure so that the exposure delivered to the film is appropriate for the film speed and brightness of the endoscopic eyepiece image.

The dual timer 188 also includes a terminal labeled TRIG, a terminal labeled DIS-1, a terminal labeled THRES-1, a terminal labeled DIS-2, a terminal labeled THRES-2, and a terminal labeled OUT-2. Connected to the terminal labeled DIS-1 is one end of a resistor 190 while the other end of the resistor 190 is connected to C+. Connected in common with the terminal labeled THRES-1 and the other end of the resistor 190 is the positive side of a capacitor 192 while the negative side of the capacitor 192 is connected to ground. The terminal of the timer 188 labeled DIS-2 is connected in common with the positive side of the capacitor 196 and one end of a resistor 194. The negative side of the capacitor 196 is connected with ground. The terminal labeled THRES-2 is connected in common with the other end of the resistor 194 the other end of which is connected in common with the positive side of the capacitor 196 and one end of a resistor 181 the other side of which is connected with the terminal labeled OUT-1 which is connected in common with both of the gates of the FET switches 198 and 220. The timer 188 is structured in a well-known manner to provide a logic 1 (high voltage) output signal at its terminal labeled OUT-1 in response to receiving a negative going trigger pulse at its terminal labeled TRIG. The duration of the logic 1 output signal at the terminal OUT-1 depends on the values of the capacitor 192 and the resistor 190. The timer 188 thus operates in this manner as a multivibrator arranged as a conventional "one-shot".

When the timer 188 receives a negative going trigger pulse at its terminal labeled TRIG, it will in addition to operating as a conventional one-shot, trigger and free run as a multivibrator in an astable mode of operation to provide a sequence of square wave pulses (FIG. 8) at its output terminal OUT-2. The duty cycle of the square wave pulses is set in accordance with the values of the capacitor 196 and the resistor 194.

A conventional electromagnetic relay 226 is also provided in the circuit 126. The relay 226 has one terminal of an internal coil 227 connected to the terminal of the dual timer 188 labeled OUT-2 while the other terminal of the internal coil 227 is connected with C+. The relay 226 is arranged in a well-known manner so that whenever the output of the dual timer 188 at its terminal OUT-2 goes high, an internal switch 229 is closed by the internal coil 227. The terminals of the switch 229 can be plugged into the light source socket 40 via a plug as shown at 90 in FIG. 1 to cause the light source 16 to provide an output strobe pulse whenever the switch 229 is closed (see FIG. 8).

A magnetic induction coil 76 is provided (see also FIG. 1) having one end connected to ground while the other end is connected to the negative end of a capacitor 182. The positive side of the capacitor 182 is connected in common with the base of a conventional NPN transistor 186 while the emitter of the transistor 186 is connected to ground and its collector is connected in common with one end of a resistor 184 and the terminal of the dual timer 188 labeled TRIG. The other end of resistor 184 is connected in common with the positive side of the capacitor 182. The magnetic induction coil 76 operates to sense when the solenoid of the camera shutter has been actuated to open the shutter to initiate exposure of the film located in the cassette 44. Thus, when the camera shutter solenoid (not shown) magnetic field is changed, it is sensed and the magnetic induction pickup coil 76 produces a negative going pulse at the terminal of the timer labeled TRIG via the foregoing arrangement.

The terminal of the timer 188 labeled OUT-1 is also connected to the base of a conventional NPN transistor 234 via a resistor 232. The emitter of the transistor 234 is connected to ground and its collector is connected in series with a lamp 230 which is in turn connected to A+ via a variable resistor 236 and a fixed resistor 228. The transistor 234, arranged in this manner, is biased on when it receives the logic 1 output signal from the terminal of the dual timer 188 labeled OUT-1 and causes the lamp 230 to provide a level of illumination which is determined by the setting of the variable resistor 236. The lamp 230 is located in a housing 86 as best seen in FIG. 2 and is positioned in front of a diffuser 130 to introduce a level of diffuse illumination into the adapter secondary light path branch 106 when the camera shutter is open. The influence that the diffused light, which is created by the lamp 238 in combination with the diffuser 130, has on the film is to reduce the characteristic slope of the film whereby the film contrast can be improved for photographing images which may have a large range of illuminance values.

Figure 7:
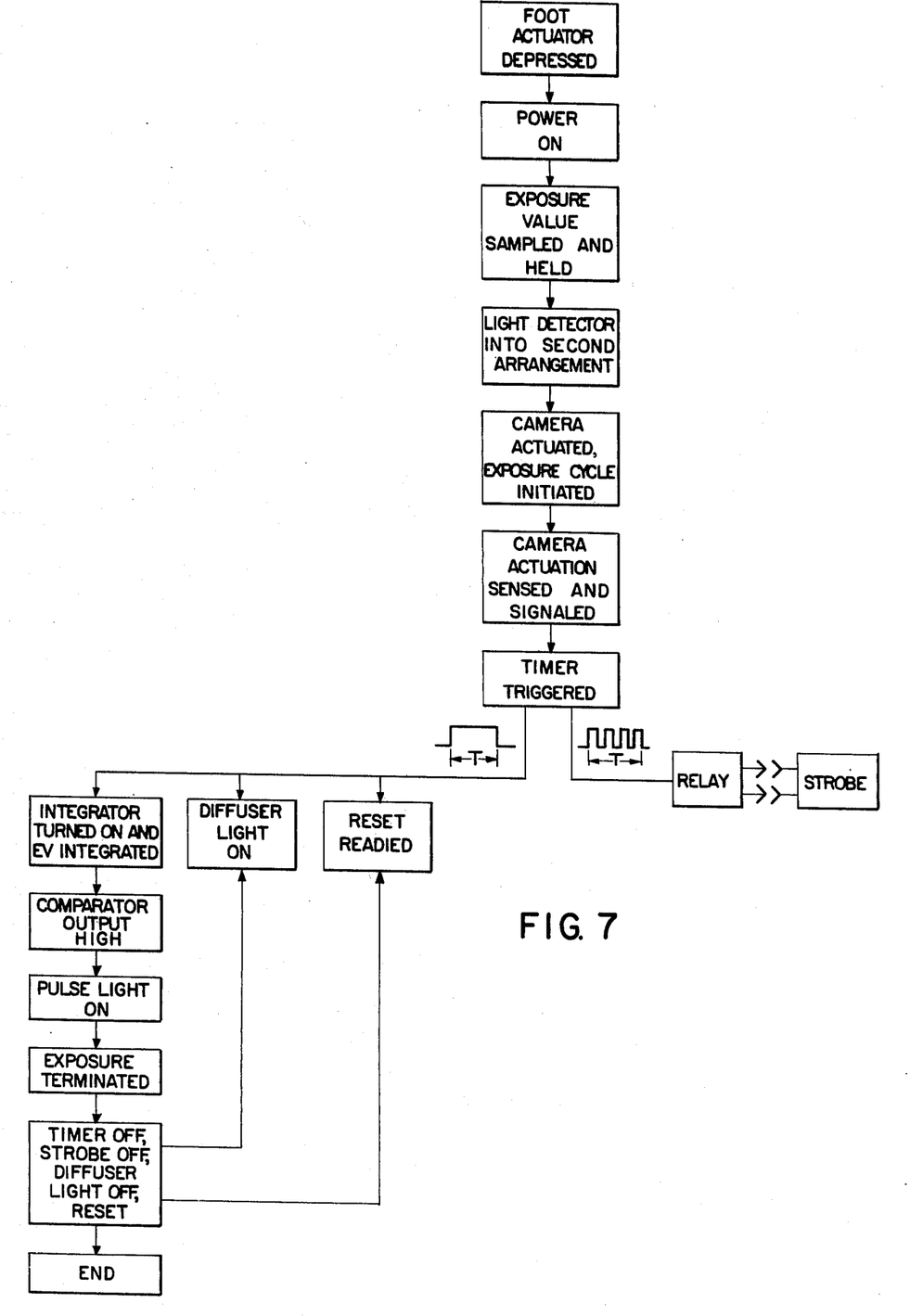
FIG. 7 is a block diagram illustrating the operating sequence for the invention.
Figure 8:
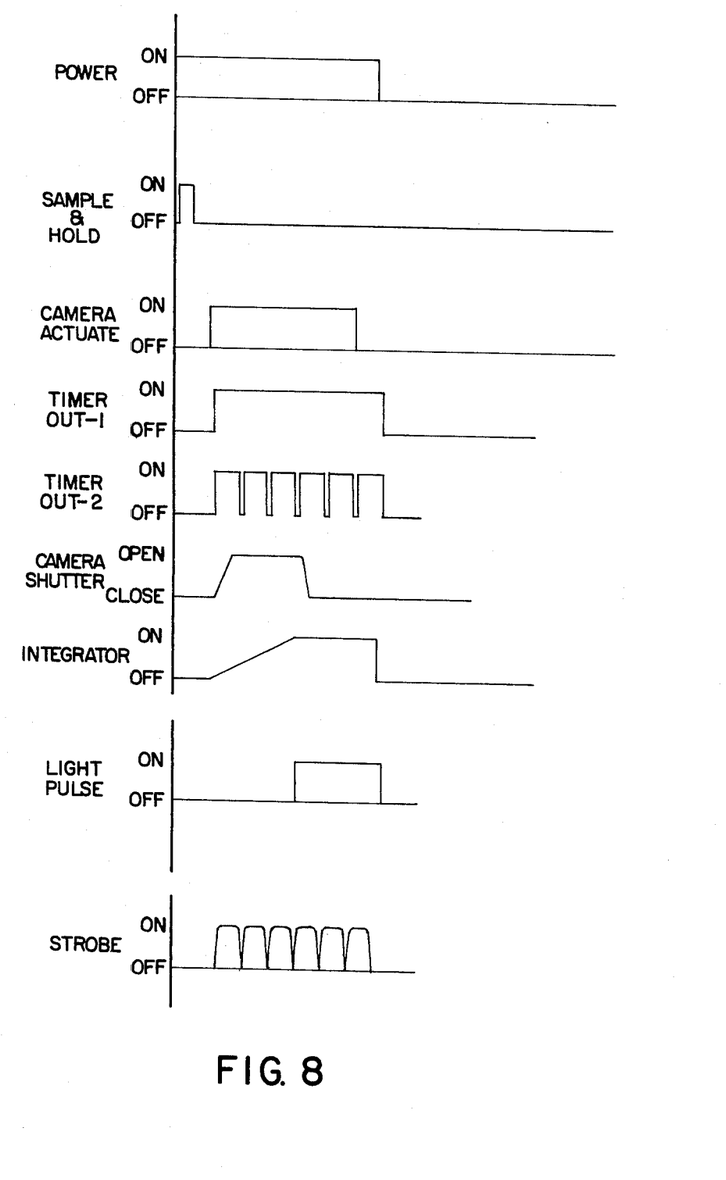
FIG. 8 is a timing diagram illustrating the time relationship between certain selected operating events for the invention, the camera, and the artificial light source of FIG. 1.

Having described the nature and operation of the various components of the circuits of FIGS. 5 and 6, the circuit 126 of FIG. 4, and the pneumatic system 133 of FIG. 3, the operation of the combination of the adapter 10, the endoscope 14, the camera 12 and the light source 16 will now be described with reference to FIGS. 7 and 8.

The combination may be operated in one of two modes—either with the object being viewed by the endoscope 14 illuminated with only the steady state continuous light output of the light source 16 or with both the steady state as well as the strobe output of a light source 16 combined to illuminate the object. The operation of the combination will first be described assuming that the strobe mode of the light source 16 is not utilized. This generally will be the mode of operation in which the invention is used and it assumes that sufficient illumination of the object can be provided by utilizing only the steady state output of the light source 16. However, if the film speed is so slow that it is required to illuminate the object with a higher intensity light, the combination may be operated with the strobe output of the light source 16 added to its steady state illumination output.

After a physician has located an object he wishes to photograph by observing the viewable image formed by the endoscope eyepiece 28, along the adapter primary light path branch 104, he then actuates the pneumatic actuator 80, preferably by foot, to create the positive pressure at its outlet. This causes the piston 134 of the cylinder 132 to move to its second position to interrupt the magnetic field of the permanent magnet 136, which forms part of the magnetically actuated reed switch 135, to cause the reed switch 135 to close to supply the A+, B+ and C+ voltages to the circuit 126. The capacitor 158 immediately then charges to the level of the output created by the operational amplifier 150 in combination with its feedback resistor 152 and the photodetector 110. The FET switch 156 is opened by the pulse received from the RC timing network as previously described. The piston 124 of the cylinder 120 then moves the yoke 112 to its second position as illustrated in phantom in FIG. 2. At this point the capacitor 158 has charged to a voltage value corresponding to the brightness of the eyepiece viewable image.

The push rod 73 of the pneumatically actuated cable release 148 is then moved to its second position wherein it depresses the camera actuator button 48 to initiate a photographic exposure cycle for the camera 12. The actuation of the camera photographic exposure cycle is detected by the magnetic proximity pickup coil 76 which creates, in a manner previously described, a negative going pulse at the terminal of the dual timer 188 labeled TRIG. The timer 188 then immediately creates a logic 1 signal at its output terminal labeled OUT-1 and also begins to create a sequence of pulses at its terminal labeled OUT-2 which in turn open and close the switch 229 of the relay 226. The logic 1 signal at the OUT-1 terminal also turns on the lamp 230 to create a diffused light level in the secondary light path branch of the adapter 106 as previously described and simultaneously closes the FET switch 198 and the FET switch 220 which in turn opens the FET switch 206. The charge stored on the capacitor 158 is then integrated by the combination of the amplifier 202 and its feedback capacitor 204 and the integrated output is compared with the internal reference voltage that is set in the comparator 216. When the voltage on the capacitor 204 has reached the internal reference voltage level of the comparator 216, the output of the comparator 216 goes high to bias the transistor 222 on and thus cause the lamp 224 to provide a highly intense light pulse which is introduced into the camera light sensing system 50 to terminate the exposure cycle of the camera 12. After the termination of the camera exposure cycle, the output of the timer 188 terminal labeled OUT-1 assumes a logic 0 state and simultaneously therewith the terminal labeled OUT-2 ceases to provide its oscillating pulse train. The lamp 230 also is turned off when the output terminal labeled OUT-1 assumes a logic 0 state. The logic 0 state at the gate of the FET switch 220 causes that switch to return to its normally open state and which in turn causes the FET switch 206 to return to its normally closed state to discharge the capacitor 204 thereby returning it or resetting it to a mode wherein it can be charged again.

It is to be noted that the internal reference voltage level of the comparator 216, as previously mentioned, can be adjusted so as to accommodate films whose speed can vary over a predetermined range of values.

If it is determined that the particular film being used has a speed which is too low to get proper exposures using only the steady state light output of the light source 16, the plug 90 can be plugged into the socket 40 to connect the relay 226 to the light source 16. When this is done, the combination operates in the same manner as previously described except that an additional level of illumination is added to the steady state illumination level provided by the light source 16 and the additional illumination provided by the pulse strobe of the light source 16 is a predetermined value. In this connection, it is to be noted that when the combination is operated utilizing both the steady state light output of the strobe 16 as well as its strobe output, the duration of the camera shutter open time is still determined by the level of the steady state illumination which is sampled and held by the circuit 126 in the manner previously described. Therefore, if it is determined that the amount of illumination provided by the combination of the steady state light output and the strobe light output of the light source 16 is too intense for proper exposure, the reference voltage level of the comparator 216 can be reduced to shorten the duration of the shutter open time to correct for overexposure which may be introduced in this manner.

Certain changes may be made in the above-described embodiment without departing from the scope of the invention and those skilled in the art may make still other changes according to the teachings of the disclosure. For example, it is obvious that the circuit 126 may be utilized separately from the adapter 10 provided that the photodetector 110 is utilized in a manner whereby it receives at least a portion of the light emanating from the image formed by an optical viewing device such as the endoscope 14. Arrangements for doing this are well-known in the art as, for example, those discussed in the description of the prior art at the beginning of this specification. Therefore, it is intended that all matter contained in the above description or shown in the accompanying drawings shall be interpreted as illustrative and not in a limiting sense.

What is claimed is:

1. An adapter for optically and mechanically coupling a photographic camera to the proximal end of an optical viewing device such as an endoscope so that the image formed by the optical viewing device can be viewed and photographed wherein the camera is of the type which includes an exposure control system having a light sensing system and which, upon actuation, automatically regulates the exposure delivered to a film in accordance with the speed rating of the film and the amount of light received by the light sensing system of the camera exposure control system and wherein the optical viewing device is of the type which has an eyepiece located at its proximal end for forming a viewable image of the object and includes means by which the object can be illuminated, said adapter comprising:

a housing section for forming a releasable generally lighttight mechanical connection with the proximal end of the optical viewing device and structured to form a branched light path having a primary branch the entrance of which optically aligns with the optical viewing device eyepiece when said housing section is connected thereto and along which the viewable image formed by the eyepiece can be directly viewed through the exit of said primary branch and having a secondary branch depending from said primary branch at a predetermined angle;

optical means disposed in said housing section for receiving light traveling along said primary light path branch and directing a portion of it into and along said secondary light path branch so that the viewable image formed by the eyepiece can be photographed through the exit of said secondary light path branch;

means for releasably attaching the camera to said housing section so that the camera objective lens is aligned in a predetermined manner with the exit of said secondary light path branch for purposes of photographing the eyepiece viewable image while the camera light sensing system is not aligned with said secondary light path branch exit;

light detecting means structured, in part, to be electrically actuated and arranged along said housing section branched light path for movement between a first at rest arrangement in which said light detecting means, upon electrical actuation, provides an output signal having an electrical characteristic which varies in a predetermined manner with the brightness of the eyepiece viewable image and in which the viewable image is visually unobstructed when observed along said primary light path branch and a second arrangement in which both said primary and secondary light path branches are unobstructed so that the eyepiece viewable image can be simultaneously viewed and photographed;

means for precluding ambient light from entering the camera light sensing system;

control means including circuit means for monitoring said light detecting means output signal while said light detecting means is in its first arrangement and determining an exposure parameter value which is appropriate for the film speed and the brightness of the eyepiece viewable image, for displacing said light detecting means from its first to its second arrangement, for actuating the camera to begin its exposure cycle, and for presenting within said light precluding means an artificial source of illumination to cause the camera light sensing system to terminate the camera exposure cycle in accordance with said exposure parameter value.

2. An adapter for optically and mechanically coupling a photographic camera to the proximal end of an optical viewing device such as an endoscope so that the image formed by the optical viewing device can be viewed and photographed wherein the camera is of the type which includes an exposure control system having a light sensing system and which, upon actuation, automatically regulates the exposure delivered to a film in accordance with the speed rating of the film and the amount of light received by the light sensing system of the camera exposure control system and wherein the optical viewing device is of the type which has an eyepiece located at its proximal end for forming a viewable image of the object and includes means by which the object can be illuminated, said adapter comprising:

a housing section for forming a releasable generally lighttight mechanical connection with the proximal end of the optical viewing device and structured to form a branched light path having a primary branch the entrance of which optically aligns with the optical viewing device eyepiece when said housing section is connected thereto and along which the viewable image formed by the eyepiece can be directly viewed through the exit of said primary branch and having a secondary branch depending from said primary branch at a predetermined angle;

optical means disposed in said housing section for receiving light traveling along said primary light path branch and directing a portion of it into and along said secondary light path branch so that the viewable image formed by the eyepiece can be photographed through the exit of said secondary light path branch;

means for releasably attaching the camera to said housing section so that the camera objective lens is aligned in a predetermined manner with the exit of said secondary light path branch for purposes of photographing the eyepiece viewable image while the camera light sensing system is not aligned with said secondary light path branch exit;

light detecting means structured, in part, to be electrically actuated and arranged along said housing section branched light path for movement between a first at rest arrangement in which said light detecting means, upon electrical actuation, provides an output signal having an electrical characteristic which varies in a predetermined manner with the brightness of the eyepiece viewable image and in which the viewable image is visually unobstructed when observed along said primary light path branch and a second arrangement in which both said primary and secondary light path branches are unobstructed so that the eyepiece viewable image can be simultaneously viewed and photographed;

means for precluding ambient light from entering the camera light sensing system;

electrically actuable circuit means structured, upon actuation, to monitor said light detecting means output signal for a predetermined time interval, sense the brightness of the image formed by the viewing device and store a signal corresponding to the image brightness; and thereafter to sense the actuation of a camera exposure cycle and substantially simultaneously therewith become responsive to said brightness related signal and provide an exposure related signal and a high intensity light pulse within said light precluding means to cause said camera light sensing system to terminate the camera exposure cycle so that the exposure delivered to the film is appropriate for the film speed and image brightness;

a switch for electrically connecting a power source to said light detecting means and said circuit means, and pneumatic control means manually actuable to, in consecutive sequence, close said switch to supply power to said light detecting means and said circuit means so that said circuit means senses the brightness of the viewing device image and stores said brightness related signal during said predetermined time interval and then to actuate the camera.

3. The adapter of claim 1 or 2 wherein said primary and secondary light path branches are arranged at right angles to one another and wherein said optical means comprises a beamsplitter arranged at an angle of 45° with respect to both said primary and secondary light path branches.

4. The adapter of claim 3 wherein said primary light path branch entrance and exits are arranged along a straight optical axis which is parallel with the optical axis of the viewing device eyepiece.

5. The adapter of claim 3 wherein the transmission and reflection characteristics of said beamsplitter are selected so that a major portion of the light which forms the viewing device eyepiece image is reflected into and along said secondary light path branch toward the camera objective lens while the remaining portion is transmitted along said primary light path branch toward the exit thereof for observation of the eyepiece image.

6. The adapter of claim 5 wherein said beamsplitter reflects at least 80 percent of the light incident thereon toward the camera objective lens.

7. The adapter of claim 1 or 2 further including an afocal telescope positioned in optical alignment with said secondary light path branch exit and structured to magnify the image presented to the camera objective lens.

8. The adapter of claim 1 or 2 wherein said light detecting means comprises:
 (a) a photodetector for providing said light detecting means output signal, said photodetector being fixedly positioned in said primary light path branch, ahead of said optical means, and arranged to not directly intercept any light from the eyepiece image and to be hidden from the view of an observer looking along said primary light path branch at the eyepiece image; and
 (b) means positioned within said secondary light path branch for intercepting at least a portion of the light reflected from said optical means into and along said secondary light path branch and directing said intercepted light onto said photodetector when said light detecting means is in its first arrangement, said light intercepting means being structured for movement between a first position corresponding to said light detecting means first arrangement and a second position, corresponding to said light detecting means second arrangement, wherein said light intercepting means is out of the path of travel of light traveling along said secondary light path branch.

9. The adapter of claim 8 wherein said light interecepting means comprises a planar mirror mounted on a pivotable yoke for movement between its said first and second positions.

10. The adapter of claim 9 wherein said photodetector includes a planar photosensitive surface and wherein said planar mirror, when in its first position is arranged with respect to said photodetector so that perpendicular lines from the center of each of said photodetector and said planar mirror surfaces are colinear.

11. The adapter of claim 10 wherein said planar mirror is structured to intercept only a given percentage of the central beam of light reflected from said optical means when said light detecting means is in its first position.

12. The adapter of claim 9 wherein said control means includes a pneumatically operated cylinder for displacing said yoke between its first and second positions.

13. The adapter of claim 1 or 2 wherein said control means comprises:
 (a) a manually actuable penumatic actuator having an outlet for, upon actuation, providing a positive pressure at said outlet;
 (b) a switch for connecting power to said circuit means;
 (c) a first pneumatic cylinder having an inlet connected to said actuator outlet, an outlet, and a piston movable between first and second positions, said cylinder being structured to respond to said positive pressure from said actuator to first displace said piston from its first position to its second position to close said switch to connect power to said circuit means and then to provide a positive pressure at its said outlet;
 (d) a second pneumatic cylinder having an inlet connected to said first cylinder outlet, a piston movable between first and second positions and connected with said light detecting means, and an outlet, said second cylinder being structured to respond to the positive pressure at said first cylinder outlet to first displace its said piston from its first to its second position to move said light detecting means from its first to its second arrangement after said switch has been closed and then to provide a positive pressure at its said outlet; and
 (e) a pneumatically actuated cable release having an inlet connected to said second cylinder outlet and a member movable in response to said positive pressure at said second cylinder outlet to actuate the camera photographic cycle via a camera actuator button.

14. The adapter of claim 1 or 2 wherein said circuit means includes means for adding at least one predetermined level of non-image forming illumination to the illumination level of the eyepiece image to add to the exposure of the film for reducing the film contrast characteristics.

* * * * *